US005282834A

United States Patent [19]

Remy

[11] Patent Number: 5,282,834

[45] Date of Patent: Feb. 1, 1994

[54] TABLE FOR STRETCHING PARAVERTEBRAL MUSCLES

[76] Inventor: Denis Remy, 28, rue du General Maistre, 52100 Saint Dizier, France

[21] Appl. No.: 916,094

[22] PCT Filed: Nov. 28, 1991

[86] PCT No.: PCT/FR91/00948

§ 371 Date: Jul. 28, 1992

§ 102(e) Date: Jul. 28, 1992

[87] PCT Pub. No.: WO92/01915

PCT Pub. Date: Jun. 11, 1992

[30] Foreign Application Priority Data

Nov. 28, 1990 [FR] France ................................ 90 14988

[51] Int. Cl.[5] .......................... A61H 1/02; A61F 5/00

[52] U.S. Cl. .................................... 606/241; 128/845; 482/35; 5/623; 182/116

[58] Field of Search .................... 5/600, 623, 624, 662; 606/241, 242; 128/845; 482/35, 142; 182/116

[56] References Cited

U.S. PATENT DOCUMENTS

| | | | |
|---|---|---|---|
| 3,491,385 | 1/1970 | Werner | 606/242 |
| 3,672,361 | 6/1972 | Fourneron | 606/241 |
| 4,102,336 | 7/1978 | Wiener et al. | 606/241 |
| 4,915,101 | 4/1990 | Cuccia | 606/244 |

FOREIGN PATENT DOCUMENTS

| | | |
|---|---|---|
| 848615 | 11/1939 | France . |
| 1226506 | 7/1960 | France . |

*Primary Examiner*—Alexander M. Grosz
*Attorney, Agent, or Firm*—Ostrolenk, Faber, Gerb & Soffen

[57] ABSTRACT

A table for effecting the stretching of the paravertebral muscles, comprising a tubular footing supporting a board (1) and formed of two vertical front legs (2) and two obliquely arranged rear legs (3), rigidly fastened on both sides to two horizontal tubes (22) constituting the edges of the table.

The board (1) is at a height which permits a patient lying prone to have his or her legs in empty space, and the table has vertical tubular handles (5) located in the extension of the rear legs (3) and two L-shaped tubular elements (6) sliding perpendicularly to the longitudinal edges (22) of the board and adapted to be locked in position, its rear legs (3) being provided with rungs (31, 32, 33; 41, 42, 43) forming two half ladders (50, 40) spaced apart by a distance (d) which permits the passage of the legs of the patient.

The table of the invention is intended for patients suffering from back pains and particularly for kinesitherapeutists.

3 Claims, 1 Drawing Sheet

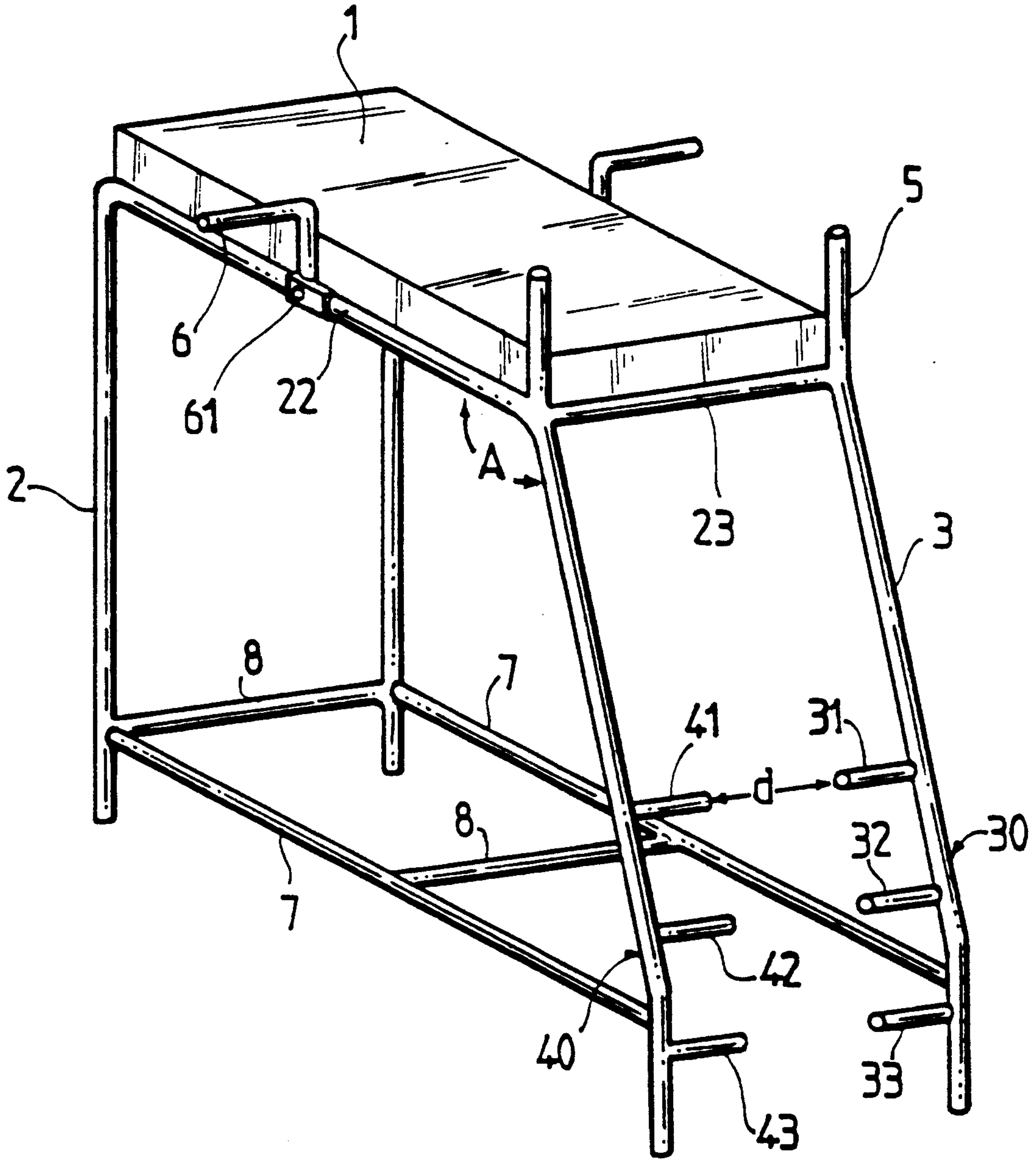
1
5
6
61
22
2
A
23
3
8
7
41
31
d
8
32
30
7
42
40
43
33

TABLE FOR STRETCHING PARAVERTEBRAL MUSCLES

The object of the present invention is a table which permits, by a simple posture, a stretching of the spinal column and therefore the alleviating of back pains.

Traditional traction tables employ sophisticated systems of pulleys and weights which are difficult to handle and at times dangerous, due to excessive traction.

The present invention makes it possible to overcome these drawbacks by proposing a table of simple design which is not dangerous in use.

The table of the invention comprises a tubular footing formed of two vertical front legs and two obliquely arranged rear legs, firmly attached on both sides to two horizontal tubes constituting the edges of the table, there being provided on the top of the unit a board positioned at a height which permits a patient lying prone to have his or her legs in empty space.

In accordance with the invention, two L-shaped tubular elements are slidably mounted on the longitudinal edges of the table, their base being firmly attached to each of said longitudinal edges and their upper part extending horizontally, on both sides of the board, which elements can be locked in position by any suitable means, for instance a screw. The function of these tubular elements is to retain the arms of the patient once the patient is installed on the table, making it possible to effect a passive stretching of the paravertebral muscles and therefore a decrease in the pressure between the vertebrae.

In accordance with the invention, two vertical handles are arranged at the upper ends of the rear legs of the table so as to permit active stretching of the paravertebral muscles when the patient grips them and extends his/her arms, pushing his/her trunk towards the front end of the table.

In accordance with a preferred embodiment of the table of the invention, each of the two rear legs of the table is provided with two or three rungs enabling the patient to climb up and lie prone, allowing his or her legs to hang in the space between the two half ladders formed by said rungs.

The invention will be better understood from a reading of the following description, which refers to the accompanying drawing in which a non-limitative embodiment is shown.

The sole FIGURE of the accompanying drawing is a perspective view of the table of the invention.

Referring to this FIGURE, it is seen that the table of the invention comprises a rectangular horizontal board 1 placed on a footing formed of two vertical front legs 2 and two rear legs 3 which are inclined towards the rear at an angle A of about 110°, assuring good stability of the unit when the patient climbs onto the table, the legs 2 and 3 being rigidly attached to horizontal longitudinal tubes 22 and horizontal transverse tubes 23.

On each of the two rear legs 3, there are fastened three inwardly directed rungs 31, 32, 33 and 41, 42, 43, each of a length of about 12 centimeters, constituting two half ladders 30 and 40 separated by a space d of about 30 centimeters, permitting the patient to have his or her legs dangling or to balance them without their being retained.

Along the longitudinal edges 22 of the board 1 there slide two tubular elements 6 of L-shape which can be locked by a screw 61 in order to restrain the patient under his/her armpits, his/her arms hanging down on both sides of the table.

The rear legs 3 are extended at their upper part by two tubular vertical handles 5 which protrude above the board 1 by about 15 centimeters. When the patient grips the handles 5 and stretches his or her arms, the trunk of the patient is pushed forward; the legs of the patient then rest against the edge of the board 1 at the level of his/her thighs, which causes a stretching of the spinal column.

As in the case of any medical table, the four legs are connected together at a short distance from the floor by longitudinal bars 7 and transverse bars 8 which assure its stability, a free space being left at the rear of the table so that the legs of the patient can dangle without being retained.

By way of illustration, for a patient of average height, the table may have a height of 120 centimeters and the board 1 a length of 80 centimeters and a width of 55 centimeters.

I claim:

1. A table for effecting a stretching of the paravertebral muscles, having a tubular footing supporting a board (1) and formed of two vertical front legs (2) and two obliquely arranged rear legs (3) which are rigidly attached on the two sides to two horizontal tubes (22) constituting the edges of the table, characterized by the fact that its board (1) is at a height permitting a patient, lying prone, to have his or her legs in open space, and by the fact that it has vertical tubular handles (5) arranged in the extension of the rear legs (3) and two L-shaped tubular elements (6) slidably positioned relative to the longitudinal edges (22) of the board (1), on which edges they are firmly secured at their base, while their upper part extends horizontally on both sides of said board (1), which elements (6) are lockable relative to said longitudinal edges.

2. A table according to claim 1, characterized by the fact that its rear legs (3) are provided with rungs (31, 32, 33; 41, 42, 43) forming two half ladders (30, 40) spaced apart by a distance (d) which permits the passage of the legs of the patient.

3. A table according to claim 2, characterized by the fact that each half ladder (30, 40) is formed of at least two rungs.

* * * * *